(12) United States Patent
Kojima et al.

(10) Patent No.: US 11,944,468 B2
(45) Date of Patent: Apr. 2, 2024

(54) MATERIAL DECOMPOSITION APPARATUS, PCCT APPARATUS, AND MATERIAL DECOMPOSITION METHOD

(71) Applicant: Hitachi, Ltd., Tokyo (JP)

(72) Inventors: Shinichi Kojima, Tokyo (JP); Kazuma Yokoi, Tokyo (JP); Isao Takahashi, Tokyo (JP); Fumito Watanabe, Tokyo (JP); Fuyuhiko Teramoto, Tokyo (JP); Taiga Gotou, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 429 days.

(21) Appl. No.: 16/876,185

(22) Filed: May 18, 2020

(65) Prior Publication Data
US 2021/0106292 A1    Apr. 15, 2021

(30) Foreign Application Priority Data

Oct. 11, 2019    (JP) ................. 2019-187946

(51) Int. Cl.
*A61B 6/03*    (2006.01)
*A61B 6/00*    (2006.01)
*A61B 6/42*    (2024.01)

(52) U.S. Cl.
CPC ............ *A61B 6/032* (2013.01); *A61B 6/4241* (2013.01); *A61B 6/5217* (2013.01); *A61B 6/545* (2013.01)

(58) Field of Classification Search
CPC ..... A61B 6/032; A61B 6/4241; A61B 6/5217; A61B 6/545; A61B 6/54
See application file for complete search history.

(56) References Cited

U.S. PATENT DOCUMENTS

| 2009/0208084 A1* | 8/2009 | Liu ........................ A61B 6/032 382/131 |
| 2017/0270692 A1 | 9/2017 | Gronberg et al. |
| 2020/0250824 A1* | 8/2020 | Yi ......................... G06T 7/0014 |

FOREIGN PATENT DOCUMENTS

JP        2018-515160 A    6/2018

OTHER PUBLICATIONS

Fredette et al., "Multi-step material decomposition for spectral computed tomography", Jul. 11, 2019, Physics in Medicine and Biology, vol. 64, (Year: 2019).*

(Continued)

*Primary Examiner* — Colin T. Sakamoto
*Assistant Examiner* — Andrew W Begeman
(74) *Attorney, Agent, or Firm* — MATTINGLY & MALUR, PC

(57) ABSTRACT

A material decomposition apparatus for performing decomposition of a material in an object. The apparatus includes a data storage section for storing correction data preliminarily generated by decomposing one of three or more materials into the other two materials, a data input section to which radiation data of the object is inputted, the radiation data being divided into a plurality of energy levels, and a decomposition processing section for repeatedly performing two-material decomposition for decomposition of the other two materials of the three or more materials using the radiation data at different energy levels and the correction data to perform decomposition of the inside of the object into the three or more materials.

6 Claims, 9 Drawing Sheets

(56) References Cited

OTHER PUBLICATIONS

Mendonca et al., "A Flexible Method for Multi-Material Decomposition of Dual-Energy CT Images" 2014, IEEE Transactions on Medical Imaging, vol. 33, No. 1, pp. 99-116 (Year: 2014).*
Chinese Office Action received in corresponding Chinese Application No. 202010479436.9 dated May 27, 2023.

* cited by examiner

*FIG.7*

| CORRECTION DATA \ ENERGY LEVEL | E1 | E2 | E3 | E4 |
|---|---|---|---|---|
| α(E) | α(E1) | α(E2) | α(E3) | α(E4) |
| β(E) | β(E1) | β(E2) | β(E3) | β(E4) |
| γ(E) | γ(E1) | γ(E2) | γ(E3) | γ(E4) |

Channel 1
Channel 2
Channel 3
⋮
Channel N

| CORREC-TION DATA \ ENERGY LEVEL | E1 | E2 | E3 | E4 |
|---|---|---|---|---|
| $\alpha(E)$ | $\alpha(E1)$ | $\alpha(E2)$ | $\alpha(E3)$ | $\alpha(E4)$ |
| $\beta(E)$ | $\beta(E1)$ | $\beta(E2)$ | $\beta(E3)$ | $\beta(E4)$ |
| $\gamma(E)$ | $\gamma(E1)$ | $\gamma(E2)$ | $\gamma(E3)$ | $\gamma(E4)$ |

MATERIAL DECOMPOSITION APPARATUS, PCCT APPARATUS, AND MATERIAL DECOMPOSITION METHOD

CLAIM OF PRIORITY

The present application claims priority from Japanese Patent Application JP 2019-187946 filed on Oct. 11, 2019, the content of which are hereby incorporated by references into this application.

BACKGROUND OF THE INVENTION

The present invention relates to a material decomposition apparatus and a material decomposition method for decomposing a material inside an object using radiation data divided into a plurality of energy levels, which has been acquired by a photon counting type detector or the like. Specifically, the present invention relates to reduction in the computation amount for the material decomposition.

BACKGROUND ART

The development of a PCCT (Photon Counting Computed Tomography) apparatus provided with the photon counting type detector as the detector of photon counting type has been in progress. Since the photon counting type detector is capable of measuring energy of the radiation photon incident on the detector, the PCCT apparatus ensures to present a medical image that contains more information than in the case of using the generally employed CT apparatus. For example, it is possible to present an energy level image as the one divided into a plurality of energy levels, and the material decomposition image as the one decomposed into the plurality of materials. Although the material decomposition image is helpful for diagnosis purpose, the image noise is increased as the number of materials subjected to the decomposition becomes large.

Japanese Unexamined Patent Application Publication (Translation of PCT Application) No. 2018-515160 discloses superposition of an image of a distributed third material derived from the three-decomposition image on the image with less image noise, which has been decomposed into a first material and a second material for suppressing an increase in the image noise as a result of an increase in the number of materials subjected to the decomposition.

SUMMARY OF THE INVENTION

In Japanese Unexamined Patent Application Publication (Translation of PCT Application) No. 2018-515160, however, the computation amount for decomposition of three or more materials is not considered. If three or more materials are subjected to decomposition, the required computation amount becomes significantly larger than the case of two-material decomposition. Accordingly, presentation of the material decomposition image requires much time, leading to interference with diagnosis.

It is an object of the present invention to provide a material decomposition apparatus and a material decomposition method, which allow reduction in the computation amount for decomposition of three or more materials using the radiation data divided into a plurality of energy levels.

The present invention provides a material decomposition apparatus for performing decomposition of a material in an object. The apparatus includes a data storage section for storing correction data preliminarily generated by decomposing one of three or more materials into the other two materials, a data input section to which radiation data of the object is inputted, the radiation data being divided into a plurality of energy levels, and a decomposition processing section for repeatedly performing two-material decomposition for decomposition of the other two materials of the three or more materials using the radiation data at different energy levels and the correction data to perform decomposition of the inside of the object into the three or more materials.

The present invention provides a material decomposition method of performing decomposition of a material in an object. The method includes a data storage step of storing correction data preliminarily generated by decomposing one of three or more materials into the other two materials, a data input step of inputting radiation data of the object, which has been divided into a plurality of energy levels, and a decomposition processing step of repeatedly performing two-material decomposition for decomposition of the other two materials of the three or more materials using the radiation data at different energy levels and the correction data to perform decomposition of the inside of the object into three or more materials.

The present invention is capable of providing the material decomposition apparatus and the material decomposition method, which allow reduction in the computation amount for decomposition of three or more materials using the radiation data divided into a plurality of energy levels.

BRIEF DESCRIPTION OF THE DRAWINGS

FIG. 7 is a view showing an example of the correction data according to the first embodiment;

DETAILED DESCRIPTION OF THE PREFERRED EMBODIMENTS

Figure 1:
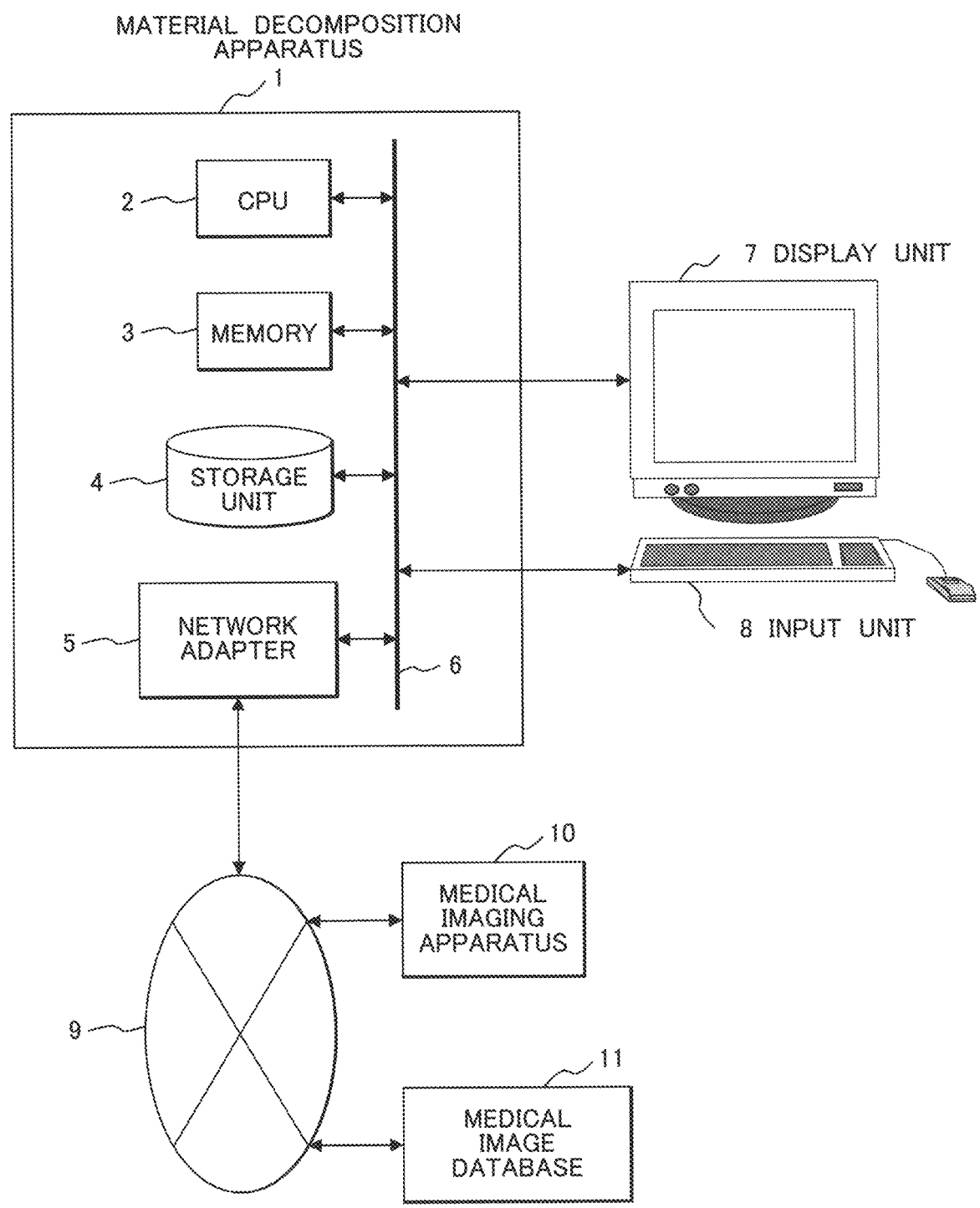
FIG. 1 is a view showing an overall structure of a material decomposition apparatus.

Hereinafter, an explanation will be made on embodiments of a material decomposition apparatus and a material decomposition method according to the present invention referring to the drawings.

First Embodiment

FIG. 1 is a view showing a hardware structure of a material decomposition apparatus 1. The material decomposition apparatus 1 includes a CPU (Central Processing Unit) 2, a memory 3, a storage unit 4, and a network adapter 5, all of which are connected to allow mutual transmission and reception of signals via a system bus 6. The material decomposition apparatus 1 is connected to a medical imaging apparatus 10 and a medical image database 11 while being allowed to mutually transmit and receive the signal via a network 9, and further connected to a display unit 7 and an input unit 8. The "mutual transmission and reception of signals" represents the state in which the signals may be transmitted and received mutually or unidirectionally from one side to the other side electrically and optically either wiredly or wirelessly.

The CPU 2 is configured to control operations of the respective components. The CPU 2 loads the program stored in the storage unit 4, and data required for executing the program in the memory 3 so that the program is executed, and performs decomposition of the material from the X-ray data divided into a plurality of energy levels. The memory 3 stores the program to be executed by the CPU 2, and the on-going status of the arithmetic processing. The storage unit 4 is configured to store the program to be executed by the CPU 2, and the data required for executing the program, specifically, in the form of a HHD (Hard Disk Drive), a SSD (Solid State Drive), and the like. The network adapter 5 is used for connecting the material decomposition apparatus 1 to the network 9, for example, the LAN (Local Area Network), telephone line, internet and the like. Various data to be processed by the CPU 2 may be transmitted to or received from the outside of the material decomposition apparatus 1 via the network 9, for example, the LAN and the like.

The display unit 7 is configured to display processing results and the like of the material decomposition apparatus 1, specifically, in the form of the liquid crystal display and the like. The input unit 8, specifically, a keyboard, a mouse, a touch panel, and the like, is an operation device which allows an operator to give an operation instruction to the material decomposition apparatus 1. The mouse may be another pointing device such as a track pad, a track ball, and the like.

The medical imaging apparatus 10 is configured to acquire a medical image of an object such as a tomographic image. The medical imaging apparatus 10 is the PCCT (Photon Counting Computed Tomography) apparatus for acquiring the X-ray data divided into a plurality of energy levels, for example, to be described later referring to FIG. 2. The medical image database 11 is a database system for storing the X-ray data which has been acquired by the medical imaging apparatus 10, and divided into the plurality of energy levels.

Figure 2:
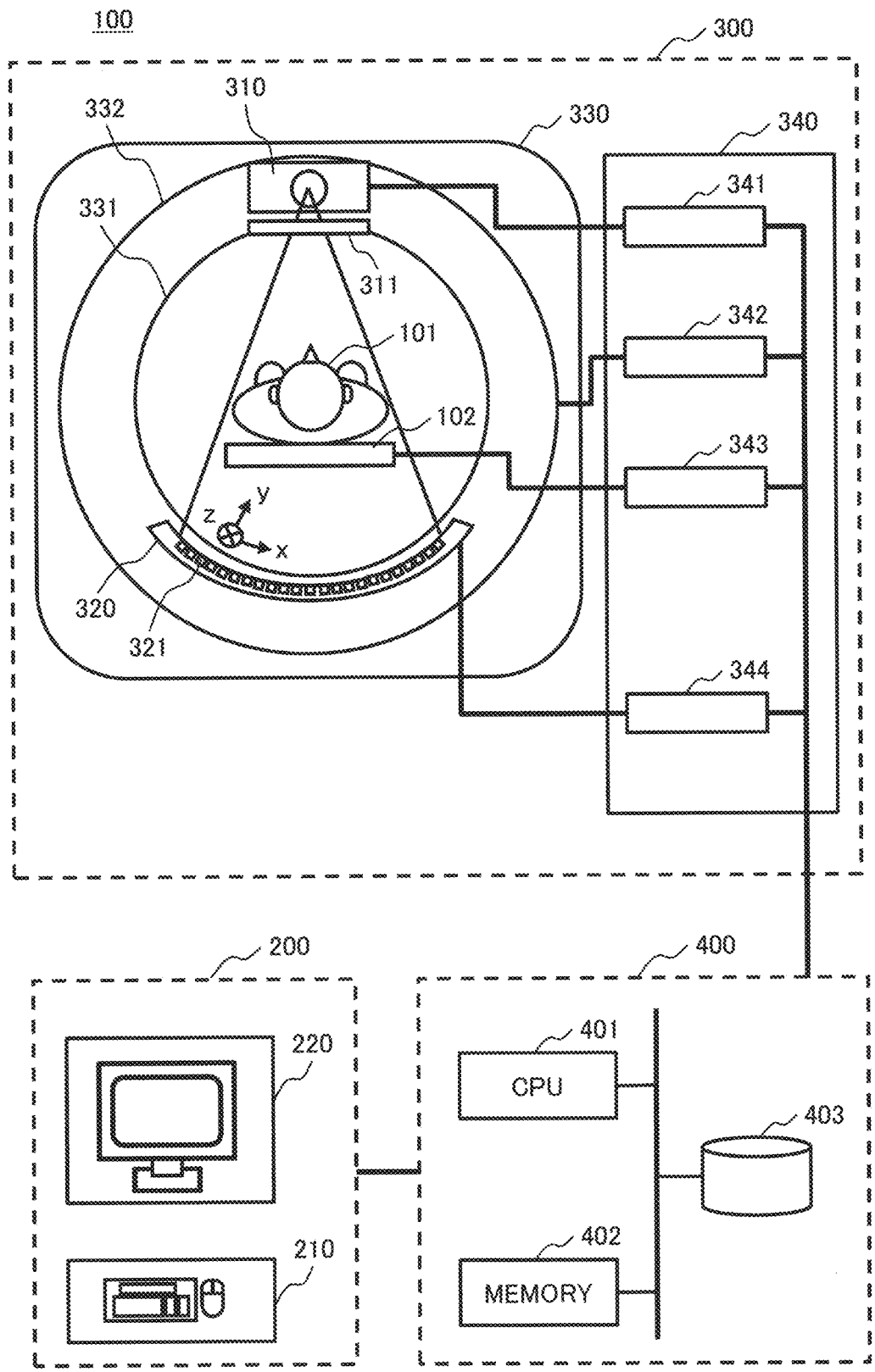
FIG. 2 is a view showing an overall structure of a PCCT apparatus as an example of a medical imaging apparatus.

An overall structure of a PCCT apparatus 100 as an example of the medical imaging apparatus 10 will be described referring to FIG. 2. The PCCT apparatus 100 includes an I/O section 200, an imaging section 300, and an integrated control section 400.

The I/O section 200 includes an input unit 210 and a monitor 220. The input unit 210 is a device to be operated by the operator for inputting imaging conditions or the like, for example, the mouse and the keyboard. The monitor 220 is a display device for outputting the inputted imaging conditions. The monitor having a touch panel function may be used as the input unit 210.

The imaging section 300 includes an X-ray source 310, an X-ray detector 320, a gantry 330, a table 102, and an imaging control unit 340 so that projection data of an object 101 is acquired at various projection angles. The projection data to be acquired is divided into a plurality of energy levels.

The X-ray source 310 is a device for irradiating the object 101 with the X-ray. A collimator 311 disposed between the X-ray source 310 and the object 101 is a device for adjusting a length of the X-ray to be irradiated to the object 101 in a z-direction.

The X-ray detector 320 is a device for detecting direct radiation as the X-ray which has not scattered but permeated through the object 101, and the X-ray detector 320 includes a plurality of detection elements 321. One thousand of the detection elements 321 are disposed from the point at which the X-ray is generated by the X-ray source 310 at equal intervals, for example, 1000 mm. The detection element 321 for detecting the X-ray outputs an electric signal in accordance with dose of the X-ray incident on the single element. The detection elements 321 arrayed on the xy plane has a size of 0.5 mm square, for example. The detection element 321 may be of indirect type constituted by combining a scintillator element and a photodiode element, or a semiconductor detection element represented by CdTe. The detection element of indirect type allows the scintillator element to generate fluorescence by the incident X-ray. The photodiode element then converts the fluorescence into the electric signal.

Figure 3:
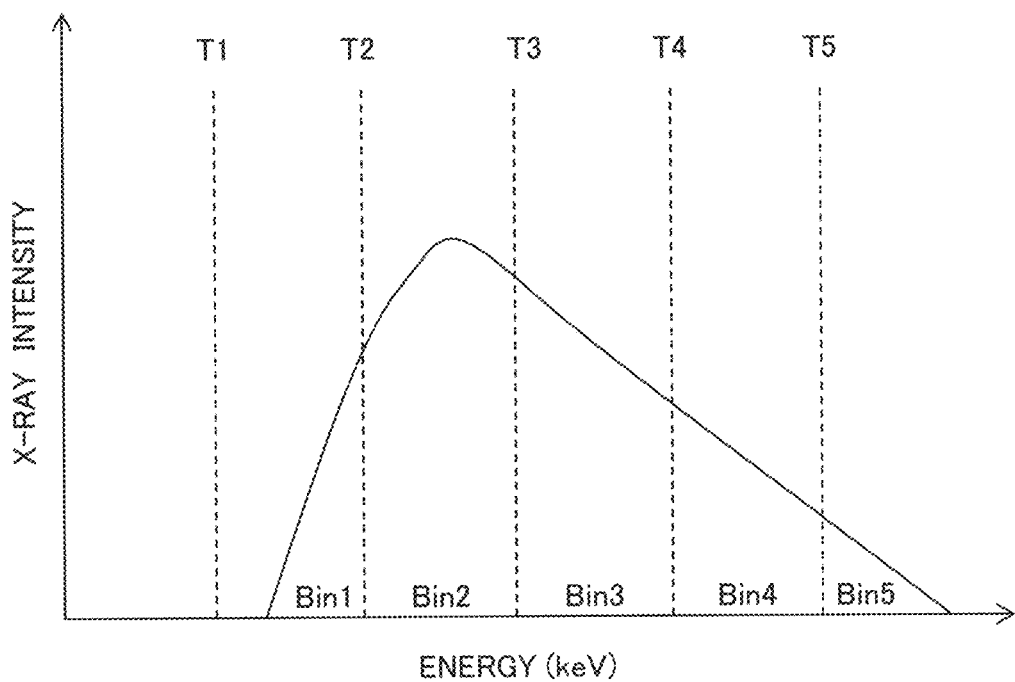
FIG. 3 is a view showing an example of an X-ray divided into a plurality of energy levels.

The detection element 321 detects the incident X-ray while being divided into the plurality of energy levels as shown in FIG. 3. FIG. 3 shows five regions divided into energy levels of T1-T2, T2-T3, T3-T4, T4-T5, and T5 onward, which are indicated as Bin1, Bin2, Bin3, Bin 4, and Bin5, respectively. It is possible to calculate the X-ray at variously combined energy levels from the detected X-ray while being divided into the plurality of divided energy levels. For example, from each X-ray intensity of Bin1, Bin2, Bin3, Bin4, and Bin5, the X-ray intensity of Bin1+Bin2 and the X-ray intensity of Bin3+Bin4+Bin5 may be calculated.

Returning to the explanation referring to FIG. 2, the gantry 330 has a circular opening 331 formed in the center so that the table 102 on which the object 101 is placed is disposed. The opening 331 has a diameter of 700 mm, for example. A rotating board 332 provided with the X-ray source 310 and the X-ray detector 320 is disposed in the gantry 330, and serves to revolve the X-ray source 310 and the X-ray detector 320 around the object 101. The table 102 moves in the z-direction for adjusting the position of the object 101 relative to the gantry 330.

The imaging control unit 340 includes an X-ray controller 341, a gantry controller 342, a table controller 343, and a detector controller 344. The X-ray controller 341 controls voltage applied to the X-ray source 310. The gantry controller 342 controls rotation of the rotating board 332 at 1.0 s/rotation, for example. The detector controller 344 controls the X-ray detection performed by the X-ray detector 320. For example, the detector controller allows the X-ray detector 320 to detect the X-ray at 0.4 degree/rotation. The table controller 343 controls movement of the table 102.

The integrated control section 400 includes a CPU 401, a memory 402, and a storage unit 403 for controlling the X-ray controller 341, the gantry controller 342, the table controller 343, and the detector controller 344, and applies various kinds of processing to the projection data acquired by the X-ray detector 320. For example, the integrated control section 400 executes the processing of reconstructing the tomographic image from the projection data acquired in accordance with the imaging condition set through the input unit 210. The tomographic image may be reconstructed for each energy level. The reconstructed tomographic image and the projection data used for the reconstruction processing may be displayed on the monitor 220, stored in the storage unit 403, and processed for each energy level.

The integrated control section 400 may serve as the material decomposition apparatus 1. In such a case, the CPU 401 corresponds to the CPU 2, the memory 402 corresponds to the memory 3, and the storage unit 403 corresponds to the storage unit 4.

Figure 4:
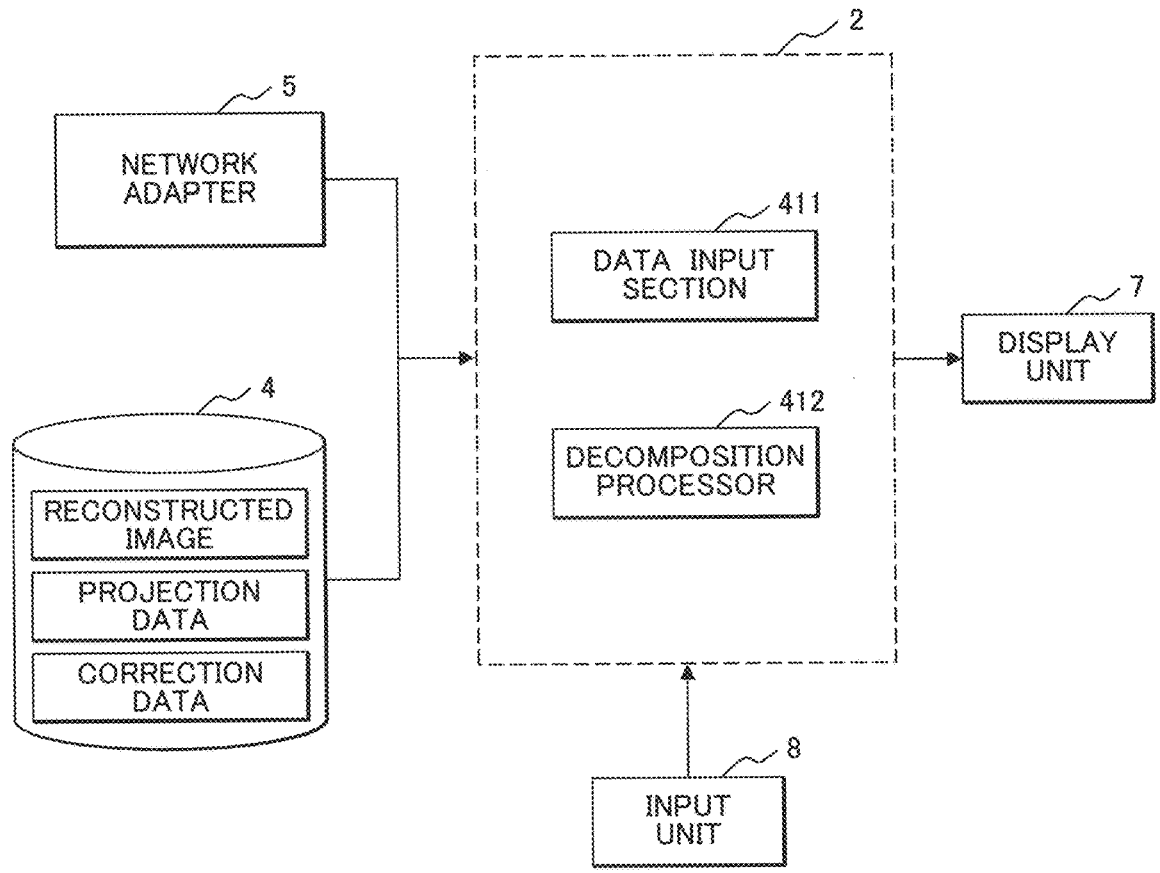
FIG. 4 is a view showing an example of a function block according to a first embodiment.

Essential parts of the embodiment will be described referring to FIG. 4. Those essential parts may be constituted by the dedicated hardware, or by the software that runs on the CPU 2. The following explanation will be made by taking the essential parts of the embodiment constituted by the software as an example. Prior to the explanation of the essential parts of the embodiment, an explanation will be made on the formula used for the three-material decomposition from the projection data divided into the plurality of energy levels.

The projection data $P(E)$ divided into the plurality of energy levels may be expressed by the following formula using radiation attenuation coefficients $\mu_A(E)$, $\mu_B(E)$, $\mu_C(E)$ of the materials A, B, C, respectively.

$$P(E) = -\mu_A(E)x_A - \mu_B(E)x_B - \mu_C(E)x_C \quad (1)$$

where E denotes X-ray energy, and each of $x_A$, $x_B$, $x_C$ denotes each length of the materials on the projection line.

The material decomposition represents the operation for acquiring each length $x_A$, $x_B$, $x_C$ of the materials from the projection data $P(E)$. As the number of materials for decomposition increases, the projection data corresponding to the number of energy levels in accordance with the number of materials is required. The computation amount for decomposition into three or more materials at a time is significantly increased. In the embodiment, in order to reduce the computation amount, the two-material decomposition as the processing for decomposition into two materials is repeatedly performed for decomposition of three or more materials. The computation amount of the two-material decomposition is smaller than the computation amount for decomposition of the three or more materials at a time. Even if the two-material decomposition is repeatedly performed, the total computation amount may still be reduced. Hereinafter, the formula used for the two-material decomposition will be shown as an exemplary case for material decomposition into three materials of A, B, and C.

A coefficient $\alpha(E)$ is incorporated into the formula (1) to rewrite the term of $\mu_C(E)x_C$ to provide the following formula for the two-material decomposition.

$$P(E) = -\mu_A(E)(x_A + (\alpha(E)\mu_C(E)/\mu_A(E))x_C) - \mu_B(E)(x_B + ((1-\alpha(E))\mu_C(E)/\mu_B(E))x_C) \quad (2)$$

Like the formula (2), a coefficient $\beta(E)$ is incorporated into the formula (1) to rewrite the term of $\mu_A(E)x_A$, and a coefficient $\gamma(E)$ is incorporated into the formula (1) to rewrite the term of $\mu_B(E)x_B$ to provide the formulae below.

$$P(E) = -\mu_B(E)(x_B + (\alpha(E)\mu_A(E)/\mu_B(E))x_A) - \mu_C(E)(x_C + ((1-\beta(E))\mu_A(E)/\mu_C(E))x_A) \quad (3)$$

$$P(E) = -\mu_C(E)(x_C + (\gamma(E)\mu_B(E)/\mu_C(E))x_B) - \mu_A(E)(x_A + ((1-\gamma(E))\mu_B(E)/\mu_A(E))x_B) \quad (4)$$

Meanwhile, upon decomposition into the materials A and B from the projection data $P(E)$, the following formula is established by setting each length of the materials A, B on the projection line to $X_{AB-A}$, $X_{AB-B}$.

$$P(E) = -\mu_A(E)X_{AB-A} - \mu_B(E)X_{AB-B} \quad (5)$$

Like the formula (5), the following formula is established upon decomposition into the materials B and C, or the materials C and A from the projection data $P(E)$. Each length of the materials B and C on the projection line for decomposition is set to $X_{BC-B}$ and $X_{BC-C}$. Each length of the materials C and A on the projection line for decomposition is set to $X_{CA-C}$ and $X_{CA-A}$.

$$P(E) = -\mu_B(E)X_{BC-B} - \mu_C(E)X_{BC-C} \quad (6)$$

$$P(E) = -\mu_C(E)X_{CA-C} - \mu_A(E)X_{CA-A} \quad (7)$$

Comparison in the terms between formulae (2) and (5), formulae (3) and (6), and formulae (4) and (7) may provide the following formulae.

$$X_{AB-A} = x_A + (\alpha(E)\mu_C(E)/\mu_A(E))x_C \quad (8)$$

$$X_{AB-B} = x_B + ((1-\alpha(E))\mu_C(E)/\mu_B(E))x_C \quad (9)$$

$$X_{BC-B} = x_B + (\beta(E)\mu_A(E)/\mu_B(E))x_A \quad (10)$$

$$X_{BC-C} = x_C + ((1-\beta(E))\mu_A(E)/\mu_C(E))x_A \quad (11)$$

$$X_{CA-C} = x_C + (\gamma(E)\mu_B(E)/\mu_C(E))x_B \quad (12)$$

$$X_{CA-A} = x_A + (1-\gamma(E))\mu_B(E)/\mu_A(E))x_B \quad (13)$$

The projection data $P_C(E_1)$ and $P_C(E_2)$, each derived from measuring the projection data $P_C(E)$ of the simple material C at different energy levels $E_1$ and $E_2$, are substituted for the formula (5). The resultant simultaneous equations are calculated to provide $X_{AB-A}$ and $X_{AB-B}$.

$$P_C(E_1) = -\mu_A(E_1)X_{AB-A} - \mu_B(E_1)X_{AB-B} \quad (14)$$

$$P_C(E_2) = -\mu_A(E_2)X_{AB-A} - \mu_B(E_2)X_{AB-B} \quad (15)$$

Values derived from calculation using the projection data $P_A(E)$, $P_B(E)$ of the materials A, B each with the known length, and the theoretical value released to NIST (National Institute of Standards and Technology) may be used for the $\mu_A(E)$ and $\mu_B(E)$. When the energy level is in the range of T1-T2, the radiation attenuation coefficient at the median (T1+T2)/2, and the radiation attenuation coefficient of the average value derived from the energy spectrum in the range of T1-T2 may be used.

Upon measurement of the projection data $P_C(E)$ of the simple material C with known length of $x_C$, $X_{AB-A}$ and $x_A=0$ calculated from the simultaneous equations of formulae (14), (15) are substituted for the formula (8) so that $\alpha(E)$ is obtained. The obtained $\alpha(E)$ is stored in the storage unit 4 as the correction data. The $X_{AB-B}$ and $x_B=0$ calculated from the projection data $P_C(E)$ are substituted for the formula (9) so that $\alpha(E)$ is obtained.

Like the case of $\alpha(E)$, the use of the projection data $P_B(E)$ of the simple material B with known length $x_B$, the projection data $P_A(E)$ of the simple material A with known length $x_A$, and the formulae (10) to (13) allows provision of $\beta(E)$ and $\gamma(E)$ so as to be stored in the storage unit 4 as correction data.

The result of two-material decomposition of the projection data $P(E)$ of the object 101 is substituted for the formulae (8) to (13) in which $\alpha(E)$, $\beta(E)$, and $\gamma(E)$ are defined. Those formulae may be used for processing three-material decomposition of the inside of the object 101. For example, substitution of $X_{AB-A}$ for the formula (8), $X_{AB-B}$ for the formula (9), and $X_{CA-C}$ for the formula (12) allows provision of the simultaneous equations relating to lengths $x_A$, $x_B$, and $x_C$. Those lengths $x_A$, $x_B$, and $x_C$ are derived from the simultaneous equations to perform the three-material decomposition of the inside of the object 101. One of energy levels in the simultaneous equations relating to $x_A$, $x_B$, and $x_C$ is made different from the other energy levels. For example, in the formulae (8) and (9), the energy level is set to $E_1$, and in the formula (12), the energy level is set to $E_2$.

Returning to the explanation referring to FIG. 4, in the embodiment, a data input section 411 and a decomposition processor 412 are provided. The projection data divided into the plurality of energy levels acquired by the PCCT apparatus 100, and the correction data $\alpha(E)$, $\beta(E)$, $\gamma(E)$ are stored in the storage unit 4. The respective components will be described hereinafter.

The projection data divided into the plurality of energy levels derived from the object 101 is inputted to the data input section 411. The data input section 411 may be configured to acquire the projection data divided into the plurality of energy levels from the PCCT apparatus 100, or read the projection data stored in the storage unit 4, the medical image database 11, and the like. The projection data of the object 101 inputted to the data input section 411 is transmitted to the decomposition processor 412.

The decomposition processor 412 performs decomposition into three or more materials of the inside of the object 101 by repeatedly performing the two-material decomposition processing using the projection data of the object 101 received from the data input section 411 and the correction data stored in the storage unit 4. The correction data used by the decomposition processor 412 are preliminarily generated using the simple material with a known thickness and property.

Figure 5:
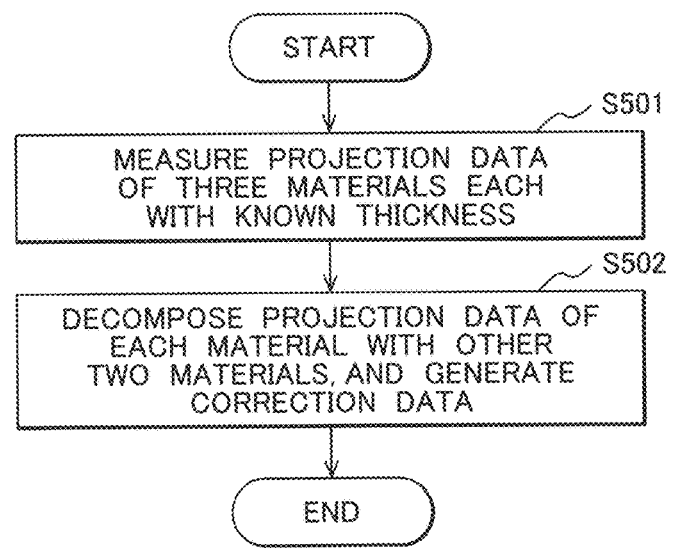
FIG. 5 is a view showing an example of a processing flow of generating correction data according to the first embodiment.

Referring to FIG. 5, an example of the processing flow of generating the correction data according to the embodiment will be described. An explanation will be made on the case of generating the correction data used for the three-material decomposition referring to FIG. 5.

(S501)

The projection data of three materials each with a known property and thickness, for example, aluminum, polytetrafluoroethylene (PTFE), and acryl is measured by the PCCT apparatus 100. In addition to those materials, material constituting the human body such as water and calcium, and the material to be introduced into the human body such as an iodine contrast agent, and such material as titanium used for the implant purpose may be measured. It is also possible to measure the contrast agent such as gold for k-edge imaging. When measuring the liquid material, a sealed vessel for sealing the liquid for measurement is used. Therefore, it is preferable to correct the data under the influence of the sealed vessel.

Figure 6:
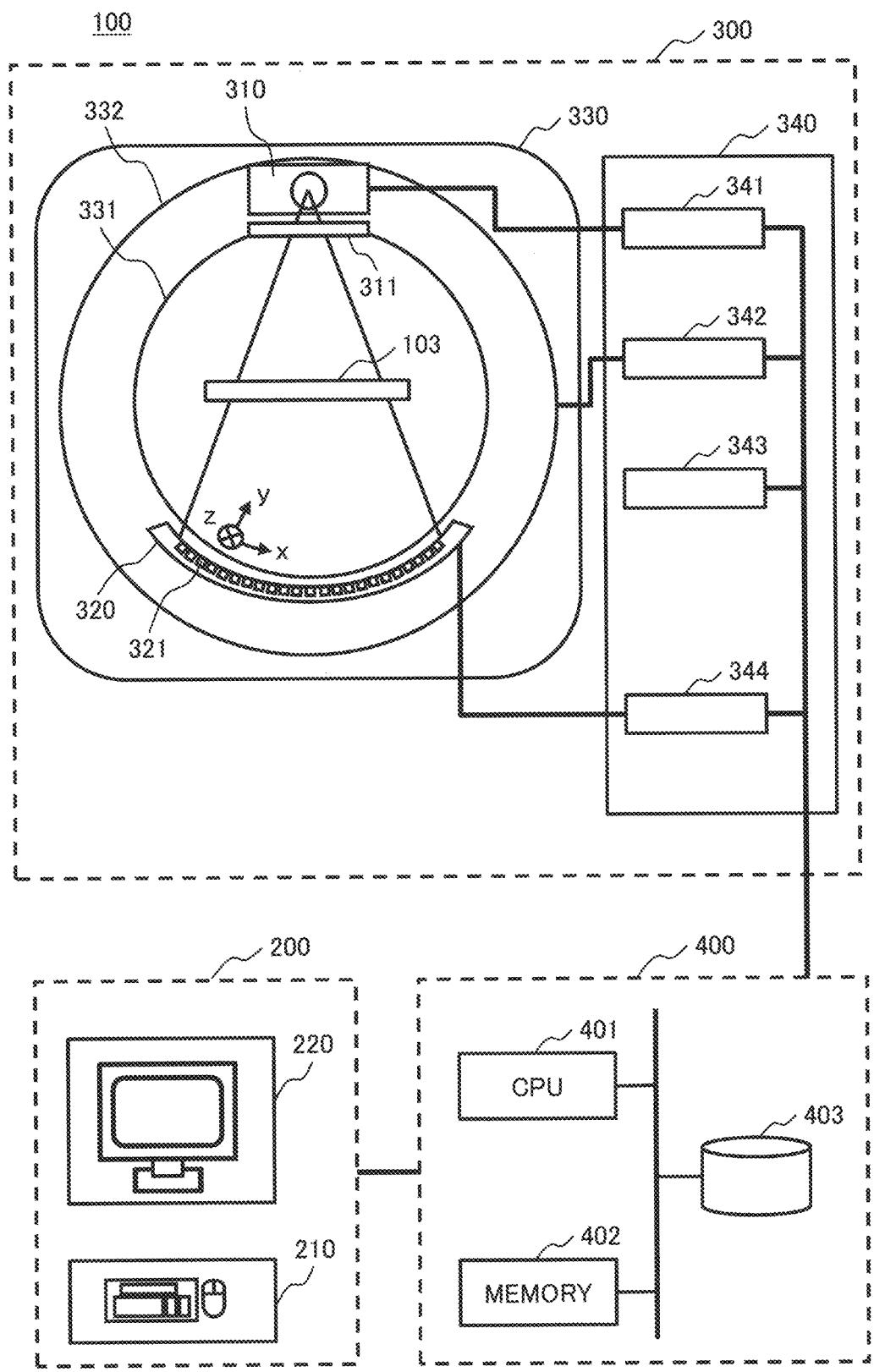
FIG. 6 is a view showing an example of a measurement material to be used for generating the correction data according to the first embodiment.

FIG. 6 shows an example of a measurement material 103 having its projection data measured. The measurement material 103 is a flat plate with a thickness of 5 cm, for example, and placed in the opening 331. The thickness of the flat plate may be changed in accordance with the material. Preferably, except the measurement material 103, nothing is placed between the X-ray source 310 and the X-ray detector 320. In the state where the measurement material 103 is placed in the opening 331, the projection data divided into the plurality of energy levels is measured without rotating the rotating board 332. If the measurement material 103 is a flat plate, the length of each of the detection elements 321 on the projection line differs depending on the angle formed by the projection line and the flat plate. Accordingly, the length is appropriately corrected for each of the detection elements 321.

It is possible to use the curved measurement material 103 so that each length of the detection elements 321 on the projection line becomes the same. Furthermore, it is also possible to acquire the projection data of the simple material with a known property and thickness through Monte Carlo simulation using a virtual measurement material on a computer. The Monte Carlo simulation allows the use of liquid such as water as the single measurement material.

(S502)

The material decomposition apparatus 1 decomposes the projection data measured in S501 into two materials other than the measured material, and generates the correction data. The specific procedure of the processing will be described as an exemplary case where the projection data $P_{aluminum}(E)$ of aluminum is decomposed into PTFE and acryl. The PTFE, acryl, and aluminum are assumed to be used as materials A, B, and C, respectively in the formulae (1) to (15).

The projection data P and $P_{aluminum}$ ($E_1$) and $P_{aluminum}$ ($E_2$) at the energy levels that have been measured with respect to the simple aluminum with a known thickness are substituted for the formula (5) to obtain the simultaneous equations such as formulae (14) and (15). From the obtained simultaneous equations, the lengths of $X_{PTFEacrylPTFE}$ and $X_{PTFEacrylacryl}$ obtained by decomposing the $P_{aluminum}(E)$ into PTFE and acryl are calculated. The $\mu_{PTFE}(E)$ and $\mu_{acryl}(E)$ are calculated from the individually measured projection data $P_{PTFE}(E)$ and $P_{acryl}(E)$ of the simple PTFE and the simple acryl, respectively. Then the calculated $X_{PTFEacrylPTFE}$, $x_{PTFE}=0$, and the thickness of the simple aluminum are substituted for the formula (8) to obtain $\alpha(E)$ as the correction data to be stored in the storage unit 4. The $\mu_{aluminum}(E)$ is calculated from $P_{aluminum}(E)$.

Like the case where the correction data $\alpha(E)$ is derived from the projection data $P_{aluminum}(E)$ of the simple aluminum, the correction data $\beta(E)$ may be derived from the projection data $\mu_{PTFE}(E)$ of the simple PTFE, and the correction data $\gamma(E)$ may be derived from the projection data $P_{acryl}(E)$ of the simple acryl. The correction data $\alpha(E)$, $\beta(E)$, and $\gamma(E)$ are obtained for each of the detection elements 321 at each energy level, and stored as indicated by a table shown in FIG. 7.

In the processing flow, one of three materials is decomposed into the other two materials so that the correction data used for the three-material decomposition is generated. The number of materials for decomposition is not limited to three as described referring to FIG. 5, but is extensible to four or more. The number of correction data pieces is extensible according to the number of materials.

An exemplified case of processing flow of three-material decomposition from the projection data of the object 101 according to the embodiment will be described referring to FIG. 8.

(S801)

The integrated control section 400 of the PCCT apparatus 100 receives the imaging conditions as those for imaging the object 101. The imaging conditions are inputted by the operator from the input unit 210. The conditions include a tube current and a tube voltage of the X-ray source 310, an opening width of the collimator 311, an imaging range in the body axis direction of the object 101, and the rotating speed of the rotating board 332. The imaging condition may be set by selecting one of the preliminarily registered multiple imaging conditions.

(S802)

The integrated control section 400 controls the X-ray controller 341, the gantry controller 342, the table controller 343, and the detector controller 344 in accordance with the imaging conditions set in S801 so that imaging of the object 101 is performed. The specific imaging procedure will be described.

The object 101 is placed on the table 102, and located at an imaging position of the gantry 330 in response to the instruction given from the integrated control section 400 to the table controller 343 for moving the table 102. At the end of positioning of the object 101, the integrated control section 400 instructs the gantry controller 342 to rotate the rotating board 332. Then the X-ray source 310 and the X-ray detector 320 start revolving around the object 101.

When the rotating board 332 establishes the constant-speed rotation, the integrated control section 400 instructs the X-ray controller 341 to irradiate X-ray from the X-ray source 310, and the detector controller 344 to allow the X-ray detector 320 to detect the X-ray. The detection data detected by the X-ray detector 320 is divided into the plurality of energy levels, and stored in the storage unit 403. The integrated control section 400 further instructs the table controller 343 to move the table 102 so that the projection data is acquired at various projection angles in the imaging range set in S801.

At the end of imaging in the imaging range, the integrated control section 400 stops the X-ray irradiation from the X-ray source 310 and the X-ray detection by the X-ray detector 320. The table 102 is then returned to a predetermined position.

In the above-described imaging procedure, the projection data of the object 101 is acquired at various projection angles while being divided into the plurality of energy levels, and stored in the storage unit 4. When performing the material decomposition using the projection data stored in the storage unit 4 and the medical image database 11, the processing in S801 and S802 does not have to be executed.

(S803)

The projection data which has been acquired while being divided into the plurality of energy levels is inputted to the data input section 411. The projection data $P_{object}(E)$ of the object 101 to be inputted to the data input section 411 may be data acquired in S802, or data preliminarily stored in the storage unit 4 or the like. The data input section 411 transmits the inputted projection data $P_{object}(E)$ to the decomposition processor 412.

The decomposition processor 412 applies the two-material decomposition to the projection data $P_{object}(E)$ multiple times, and uses the data derived from the two-material decomposition to calculate each length of three materials on the projection line, that is, to execute three-material decomposition. The specific procedure will be described, taking the use of three materials, that is, aluminum, PTFE, and acryl as an example. In the formulae (1) to (15), the materials A, B, and C are PTFE, acryl, and aluminum, respectively.

Using at least two of the formulae (5) to (7), the two-material decomposition is applied to the projection data $P_{object}(E)$ at least twice. For example, lengths of $X_{PTFEacrylPTFE}$ and $X_{PTFEacrylacryl}$ obtained by decomposing the $P_{object}(E)$ into PTFE and acryl are calculated using the formula (5). Lengths of $X_{aluminumPTFEaluminum}$ and $X_{aluminumPTFEPTFE}$ obtained by decomposing the $P_{object}(E)$ into aluminum and PTFE are calculated using the formula (7).

Then the $X_{PTFEacrylPTFE}$ and the correction data $\alpha(E)$ are substituted for the formula (8), the $X_{PTFEacrylacryl}$ and the correction data $\alpha(E)$ are substituted for the formula (9), the $X_{aluminumPTFEaluminum}$ and the correction data $\gamma(E)$ are substituted for the formula (12) to provide the simultaneous equations relating to the lengths of $x_{PTFE}$, $x_{acryl}$, $x_{aluminum}$. The correction data $\alpha(E)$, $\gamma(E)$ may be read from the storage unit 4, and $\mu_{PTFE}(E)$, $P_{acryl}(E)$, and $P_{aluminum}(E)$ may be calculated from $P_{PTFE}(E)$, $P_{acryl}(E)$, and $P_{aluminum}(E)$ acquired upon generation of the correction data, respectively. Alternatively, the theoretical value may be used. At least one of the simultaneous equations employs the energy level different from that of the other equations.

The lengths $x_{PTFE}$, $x_{acryl}$, and $x_{aluminum}$ are derived from the acquired simultaneous equations to perform the three-material decomposition.

Execution of the procedure as described above allows the projection data at each projection angle to be decomposed into three materials of PTFE, acryl, and aluminum. The projection data for each material derived from the decomposition is stored in the storage unit 4.

The two-material decomposition may be applied to the $P_{object}(E)$ into acryl and aluminum using the formula (6). When using the formula (6), the $x_{acrylaluminumacryl}$ and $X_{acrylaluminumaluminum}$ are calculated. At least one of the formulae (10) and (11) is used for the simultaneous equation to be used for performing the three-material decomposition.

(S804)

The material decomposition apparatus 1 or the integrated control section 400 of the PCCT apparatus 100 reconstructs the tomographic image for each material using the projection data for each material decomposed in S803. The Feldkamp method and successive approximation reconstruction method may be used for reconstruction. The reconstructed tomographic image for each material is displayed on the display unit 7 or the like for diagnosing the object 101. The tomographic images for the respective materials may be displayed while being mutually superposed.

The processing flow as described above allows provision of the projection data for each of three decomposed materials from the projection data of the object 101, which has been acquired while being divided into the plurality of energy levels. In the processing flow of the embodiment, the two-material decomposition requiring relatively small computation amount is utilized. This allows reduction in the computation amount for the three-material decomposition. As a result, the arithmetic time required for the three-material decomposition may be reduced to approximately ⅓ of the conventional time.

Figure 8:
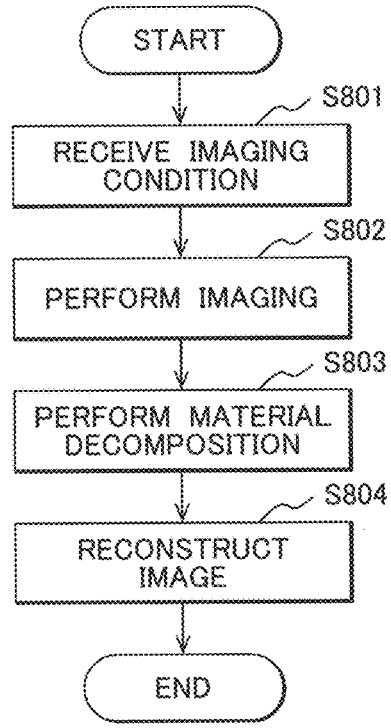
FIG. 8 is a view showing an example of a processing flow of material decomposition according to the first embodiment.

The number of materials for decomposition is not limited to three but is extensible to four or more as described referring to FIG. 8. The number of simultaneous equations is extensible accordingly. Assuming that the number of materials for decomposition is N, the number of times of the two-material decomposition performed in S803 may be N−1 or more. Limiting the number of times of the two-material decomposition can further decrease the computation amount.

Second Embodiment

In the first embodiment, an explanation has been made on decomposition of the projection data of the object 101 into three or more materials. In this embodiment, an explanation will be made on decomposition of image data of the object 101 into three or more materials. The components each with the same function as those described in the first embodiment will be designated with the same signs, and explanations thereof, thus will be omitted.

Figure 9:
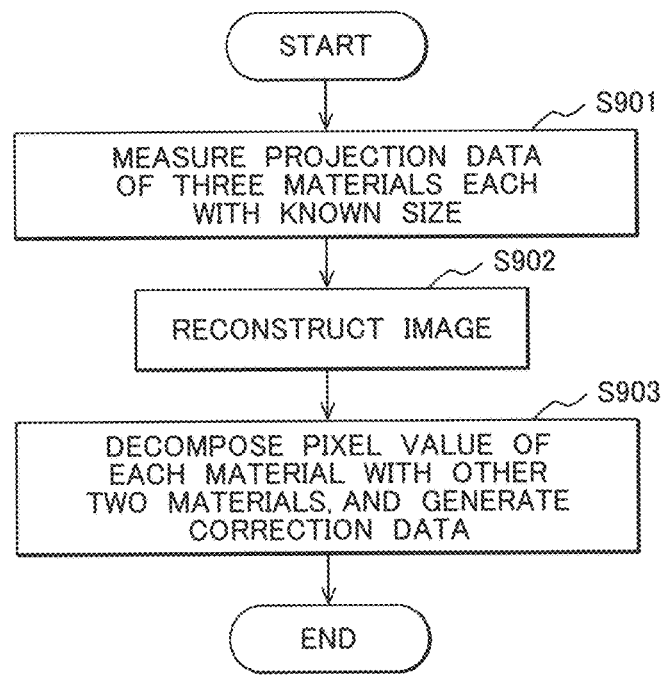
FIG. 9 is a view showing an example of a processing flow of generating correction data according to a second embodiment.

An exemplary case of the processing flow of generating the correction data according to the embodiment will be described referring to FIG. 9. FIG. 9 represents the case where the correction data used for the three-material decomposition is generated.
(S901)
The PCCT apparatus 100 measures the projection data of three materials each with a known property and size, for example, aluminum, polytetrafluoroethylene (PTFE), and acryl. In addition to those materials, the material constituting the human body such as water and calcium, and the material to be introduced into the human body such as an iodine contrast agent, and such material as titanium used for the implant purpose may be measured. It is also possible to measure the contrast agent such as gold for k-edge imaging.

Figure 10:
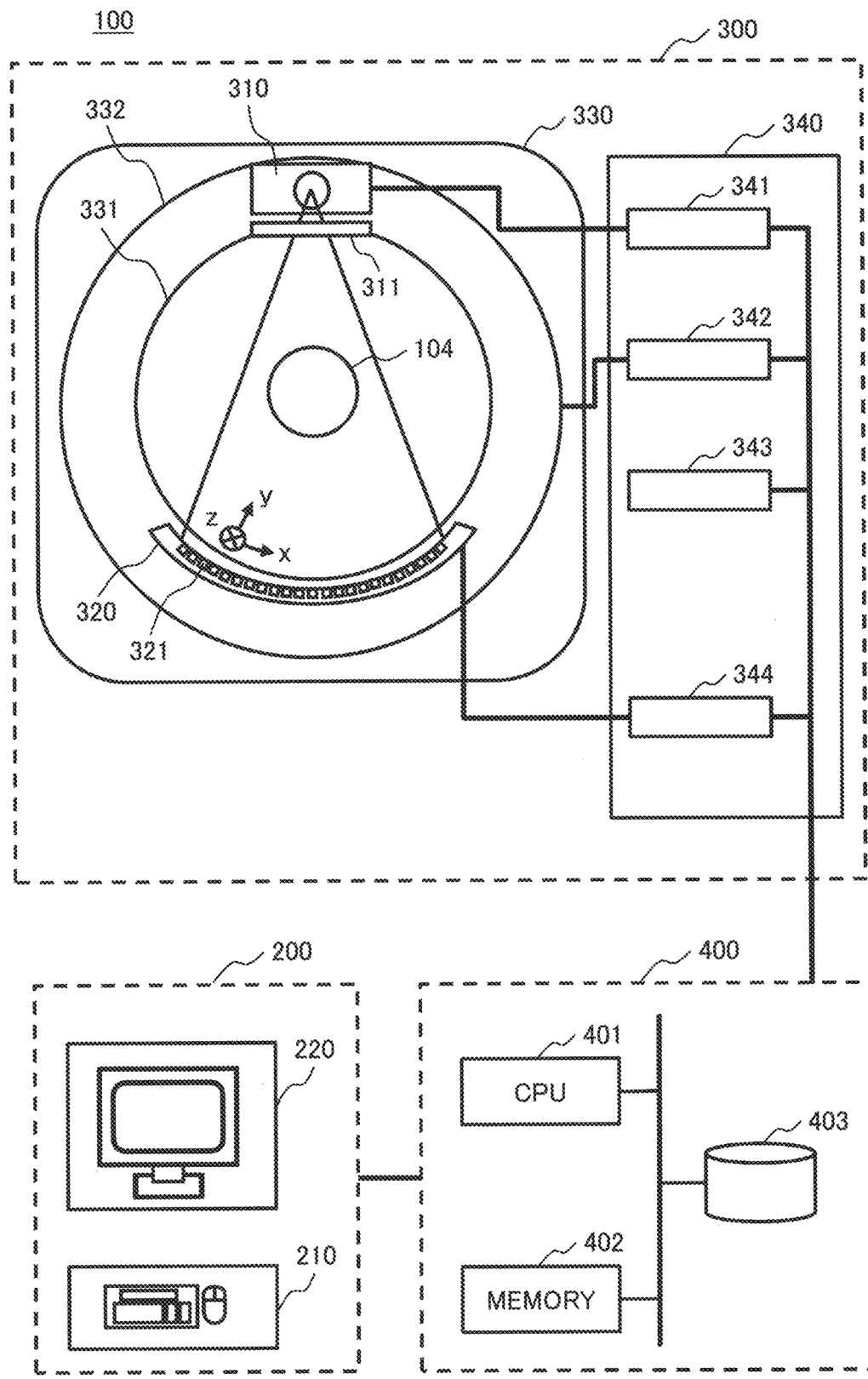
FIG. 10 is a view showing an example of a measurement phantom to be used for generating the correction data according to the second embodiment.

FIG. 10 shows an example of a measurement phantom 104 as a phantom of the material having its projection data measured. The measurement phantom 104 has a columnar shape with a diameter of 5 cm, for example, and is placed in the center of the opening 331. The diameter of the column may be changed for each of the materials. Preferably, except the measurement phantom 104, nothing is placed between the X-ray source 310 and the X-ray detector 320. In the state where the measurement phantom 104 is placed in the center of the opening 331, the projection data divided into the plurality of energy levels is measured while having the rotating board 332 rotated.

It is possible to acquire the projection data of the simple material with a known property and size by performing Monte Carlo simulation using the virtual measurement phantom on the computer. The Monte Carlo simulation allows the use of liquid such as water as the single measurement material.
(S902)
The material decomposition apparatus 1 or the integrated control section 400 of the PCCT apparatus 100 reconstructs the tomographic image for each material using the projection data acquired in S901. The Feldkamp method and successive approximation reconstruction method may be used for reconstruction.
(S903)
The material decomposition apparatus 1 decomposes a pixel value of the tomographic image reconstructed in S902 into two materials other than the material measured in S901, and generates correction data. A pixel value p of the tomographic image is expressed by the following formula instead of the formula (1).

$$(p+1000)\mu_{water}(E)/1000 = \mu_A(E)p_A + \mu_B(E)p_B + \mu_C(E)p_C \quad (16)$$

where $\mu_{water}(E)$ denotes the radiation attenuation coefficient of water, $\mu_A(E)$, $\mu_B(E)$, and $\mu_C(E)$ denote radiation attenuation coefficients of the materials A, B, and C, and $p_A$, $p_B$, and $p_C$ denote pixel values of tomographic images of the materials A, B, and C, respectively.

In comparison with the formula (1) with the formula (16), the P(E) is replaced with $(p+1000)\mu_{water}(E)/1000$, and $x_A$, $x_B$, and $x_C$ are replaced with $p_A$, $p_B$, and $p_C$, respectively so that the correction data $\alpha(E)$, $\beta(E)$, and $\gamma(E)$ are derived from the formulae (5) to (13) like the case of the projection data. The correction data $\alpha(E)$, $\beta(E)$, and $\gamma(E)$ are derived for each energy level, and stored as indicated by a table as shown in FIG. 11.

Any one of the three materials is decomposed into the other two materials in the above-described processing flow so as to generate the correction data used for performing the three-material decomposition. The number of materials for decomposition is not limited to three as described referring to FIG. 9 but is extensible to four or more. The number of correction data is extensible according to the extended number of the materials.

Figures 11, 12:
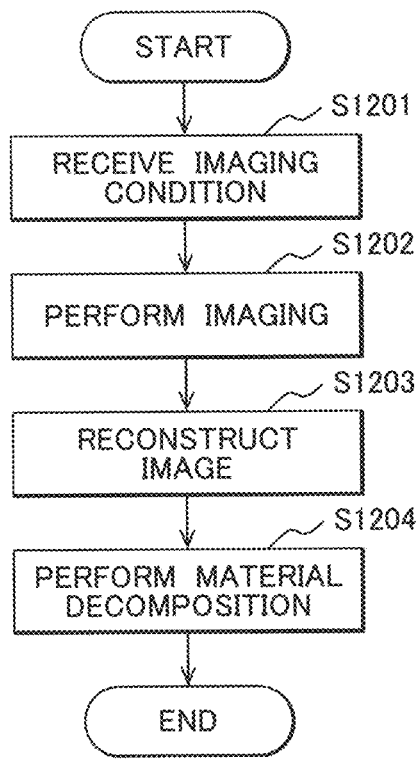
FIG. 11 is a view showing an example of the correction data according to the second embodiment.
FIG. 12 is a view showing an example of a processing flow of material decomposition according to the second embodiment.

Referring to FIG. 12, an exemplary case of processing flow of performing the three-material decomposition from the image data of the object 101 according to the embodiment will be described.
(S1201)
The integrated control section 400 of the PCCT apparatus 100 receives imaging conditions as those for imaging the object 101 like the processing in S801.
(S1202)
The integrated control section 400 controls the X-ray controller 341, the gantry controller 342, the table controller 343, and the detector controller 344 in accordance with the imaging conditions set in S1201 so that imaging of the object 101 is performed like the processing in S802. In this step, the projection data of the object 101 divided into the plurality of energy levels is acquired.
(S1203)
The material decomposition apparatus 1 or the integrated control section 400 of the PCCT apparatus 100 reconstructs the tomographic image of the object 101 for each energy level using the projection data acquired in S1202. The Feldkamp method and successive approximation reconstruction method may be used for reconstruction.
(S1204)
The tomographic image of the object 101 which has been reconstructed for each energy level is inputted to the data input section 411. The tomographic image of the object 101 inputted to the data input section 411 may be the image reconstructed in S1203, or the image preliminarily stored in the storage unit 4. The data input section 411 transmits the inputted tomographic image of the object to the decomposition processor 412.

The decomposition processor 412 applies the two-material decomposition to the pixel value of the tomographic image of the object 101 multiple times, and calculates the pixel values of three materials, that is, performs the three-material decomposition using the pixel values derived from the two-material decomposition. In comparison with the formula (1) with the formula (16), the P(E) is replaced with $(p+1000)\mu_{water}(E)/1000$, and $x_A$, $x_B$, and $x_C$ are replaced with $p_A$, $p_B$, and $p_C$, respectively so that the three-material decomposition may be performed in the manner similar to the case of the projection data. The detailed description of the processing, thus, will be omitted.

The processing flow as described above allows provision of the tomographic image for each of three decomposed materials from the tomographic image of the object 101, which has been acquired while being divided into the plurality of energy levels. In the processing flow of the embodiment, the two-material decomposition requiring relatively small computation amount is utilized. This allows reduction in the computation amount for the three-material decomposition. The number of the materials to be decomposed is not limited to three as described referring to FIG. 12 but extensible to four or more. The number of the simultaneous equations is extensible accordingly.

In the first embodiment in which the material decomposition of the projection data is performed, it is necessary to correct the non-linear response of the X-ray detector 320 resulting from pile-up and charge-sharing by performing the material decomposition and successive computation. Meanwhile, in this embodiment, the correction to the non-linear response may be separated from the material decomposition. Compared with the first embodiment, the embodiment for the material decomposition of the image data is capable of reducing the time required for presenting the material decomposition image.

Embodiments of the material decomposition apparatus and the material decomposition method according to the present invention have been described. The material decomposition apparatus and the material decomposition method according to the present invention are not limited to the embodiments as described above but may be implemented by modifying the components without departing from the scope of the present invention. The plurality of components as disclosed in the embodiments may be arbitrarily combined. Furthermore, it is also possible to delete some components from all those constituting the structure as described in the embodiments.

REFERENCE SIGNS LIST

1 . . . material decomposition apparatus,
2 . . . CPU,
3 . . . memory,
4 . . . storage unit,
5 . . . network adapter,
6 . . . system bus,
7 . . . display unit,
8 . . . input unit,
10 . . . medical imaging apparatus,
11 . . . medical image database,
100 . . . PCCT apparatus,
101 . . . object,
102 . . . table,
103 . . . measurement material,
104 . . . measurement phantom,
200 . . . I/O section,
210 . . . input unit,
220 . . . monitor,
300 . . . imaging section,
310 . . . X-ray source,
311 . . . collimator,
320 . . . X-ray detector,
321 . . . detection element,
330 . . . gantry,
331 . . . opening,
332 . . . rotating board,
340 . . . imaging control unit,
341 . . . X-ray controller,
342 . . . gantry controller,
343 . . . table controller,
344 . . . detector controller,
400 . . . integrated control section,
401 . . . CPU,
402 . . . memory,
403 . . . storage unit,
411 . . . data input section,
412 . . . decomposition processor

What is claimed is:

1. A material decomposition apparatus for performing decomposition of a material in an object, comprising:
a processor;
a first memory coupled to the processor; and
a second memory coupled to the processor,
wherein the first memory stores instructions that when executed by the processor, configure the processor to:
store, in the second memory, a plurality of correction data preliminarily generated for each combination of the three or more materials, each of a plurality of detection elements and each energy level by individually decomposing each one of three or more materials into the other respective materials of the three or more materials,
input radiation data of the object, the radiation data being divided into the plurality of energy levels, and
repeatedly perform two-material decomposition for decomposition of the three or more materials using the radiation data at different energy levels and using the stored correction data of each detection element for each energy level to perform decomposition of the inside of the object into the three or more materials.

2. The material decomposition apparatus according to claim 1,
wherein when the number of the materials for decomposition is N, the number of times of the two-material decomposition performed by the decomposition processing section is N−1.

3. The material decomposition apparatus according to claim 1, wherein the radiation data is projection data of the object.

4. The material decomposition apparatus according to claim 1,
wherein the radiation data is image data of the object.

5. A PCCT apparatus comprising the material decomposition apparatus according to claim 1.

6. A material decomposition method of performing decomposition of a material in an object, comprising:
storing, in a memory, a plurality of correction data preliminarily generated for each combination of the three or more materials, each of a plurality of detection elements and each energy level by individually decomposing each one of three or more materials into the other respective materials of the three or more materials;
inputting radiation data of the object, which has been divided into the plurality of energy levels; and
repeatedly performing, with a processor, two-material decomposition for decomposition of the three or more materials using the radiation data at different energy levels and using the stored correction data of each detection element for each energy level to perform decomposition of the inside of the object into three or more materials.

* * * * *